United States Patent [19]

Kopunek et al.

[11] Patent Number: 4,892,481
[45] Date of Patent: Jan. 9, 1990

[54] DENTAL COMPOSITE CARRIER AND COMPOSITE PACKAGE

[75] Inventors: Thomas V. Kopunek, Lewes, Del.; Douglas D. Bennett, Cambridge, Md.

[73] Assignee: Dentsply Research & Development Corp., Milford, Del.

[21] Appl. No.: 215,657

[22] Filed: Jul. 6, 1988

Related U.S. Application Data

[62] Division of Ser. No. 35,574, Apr. 7, 1987, Pat. No. 4,767,325.

[51] Int. Cl.$^4$ .............................................. A61C 5/04
[52] U.S. Cl. .................................... 433/90; 206/562; 206/564
[58] Field of Search ............................ 433/90, 89, 83; 220/23.8, 21; 206/562, 564, 563

[56] References Cited

U.S. PATENT DOCUMENTS

| 3,509,993 | 5/1970 | Michel | 220/21 |
| 4,218,215 | 8/1980 | Lancellotti | 433/90 |
| 4,391,590 | 7/1983 | Dougherty | 433/90 |
| 4,479,781 | 10/1984 | Herold et al. | 433/90 |

OTHER PUBLICATIONS

Hager & Werken Katalog, (2 pages), 1984-85.
Photocopies of a Premier Carrier, (2 pages).
Design Application No. 77843, (5 pages).

Primary Examiner—Robert Peshock
Attorney, Agent, or Firm—David E. Wheeler; Edward J. Hanson, Jr.

[57] ABSTRACT

A dental composite carrier and a packaging means for a composite used for posterior restorations in a tooth is provided. The composite carrier comprises a handle having a lever with a jaw on one end, and the package comprises individual incremental portions of composite material contained in ampules, and a number of ampules packaged in a tray. The composite carrier is used to pick an ampule out of the tray, carry it to a tooth, and deliver it into a cavity in the tooth. Optionally, the handle may have a condenser on its opposite end to be used for packing and smoothing the composite in the tooth.

5 Claims, 2 Drawing Sheets

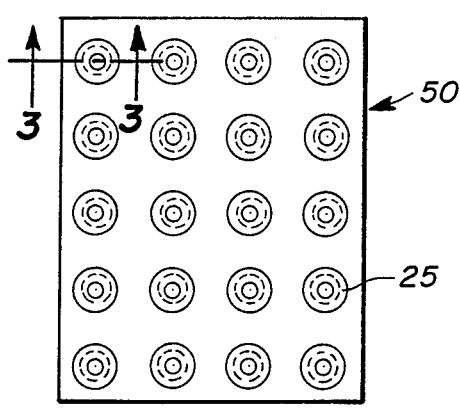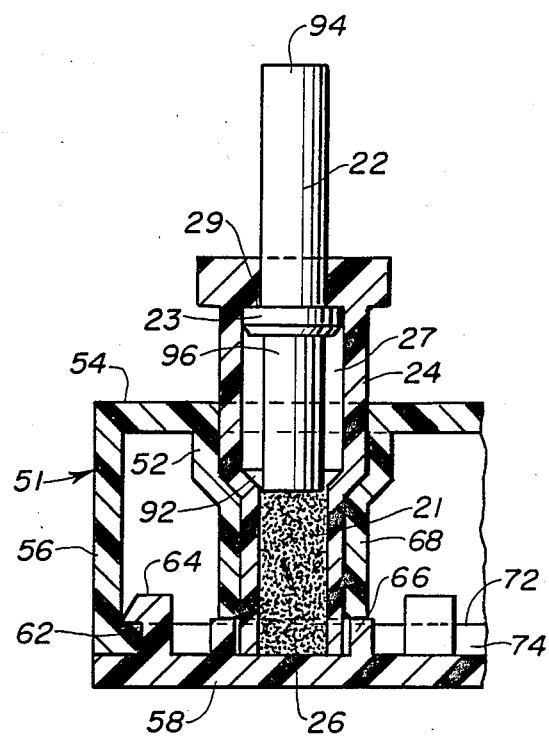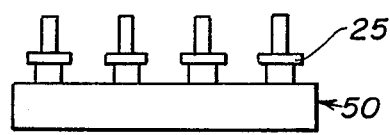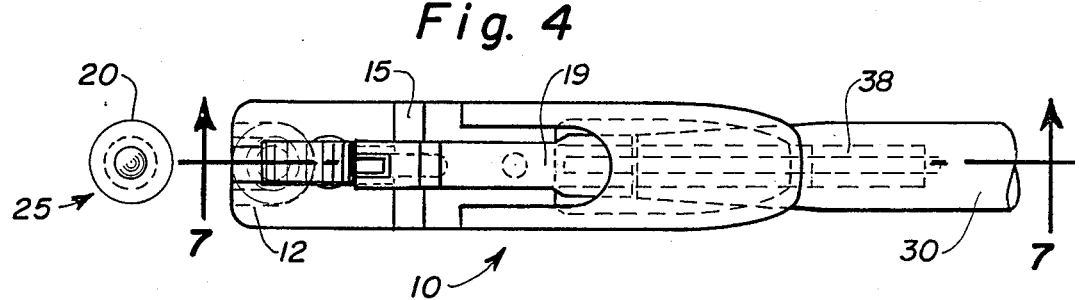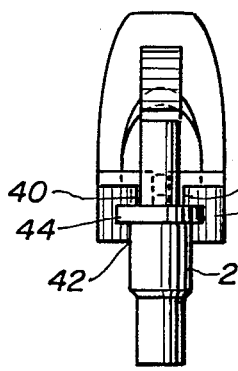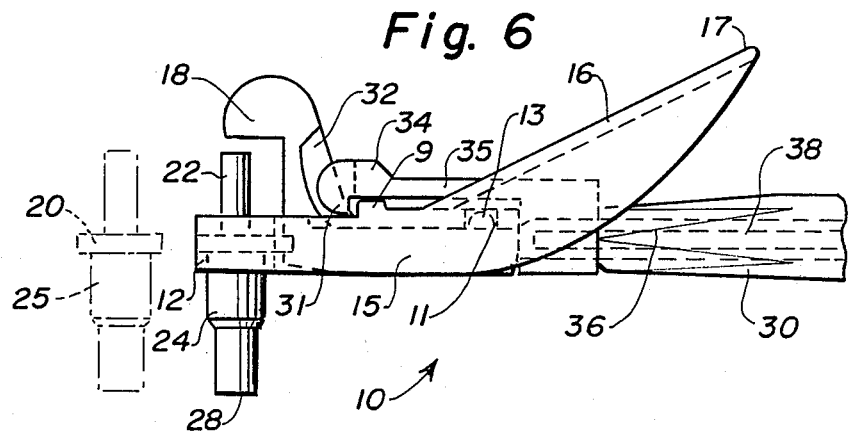

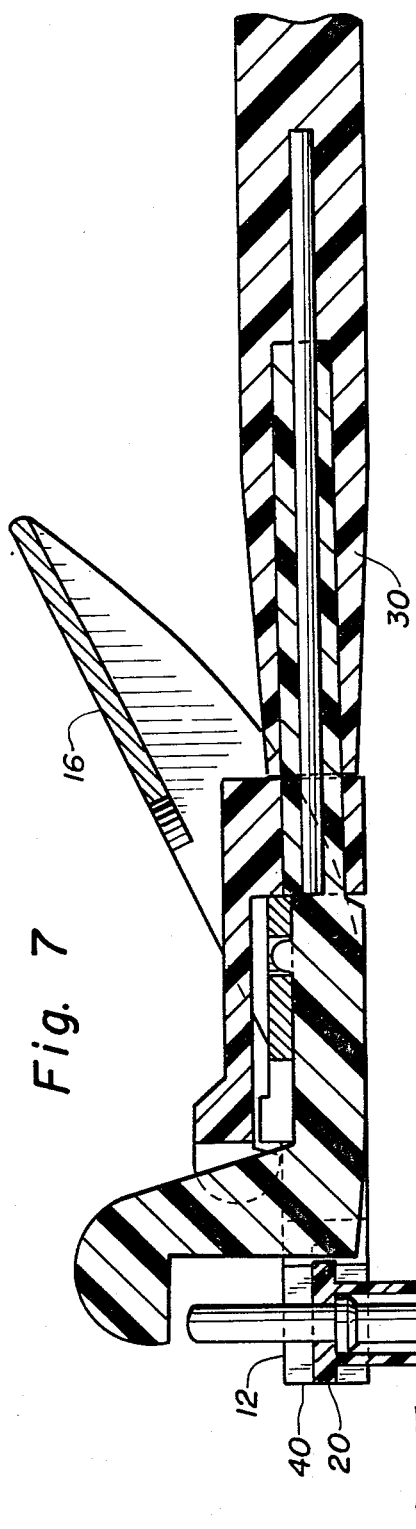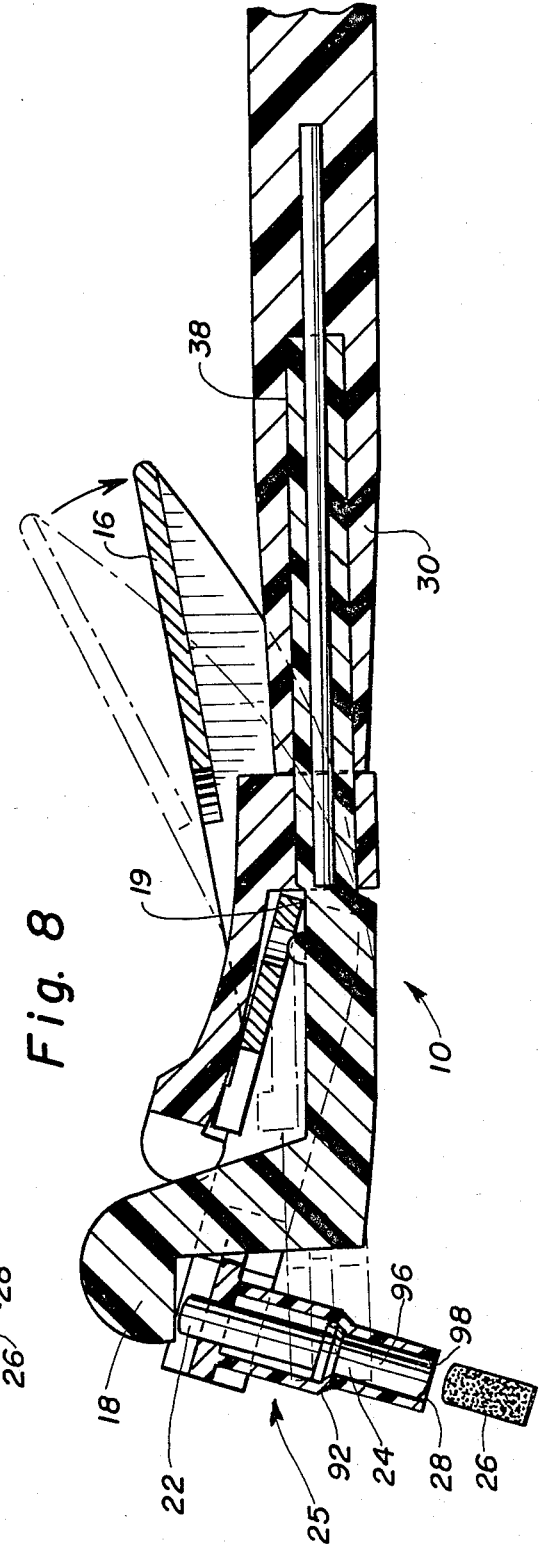

DENTAL COMPOSITE CARRIER AND COMPOSITE PACKAGE

This is a division of application Ser. No. 035,574, filed Apr. 7, 1987, now U.S. Pat. No. 4,767,325.

BACKGROUND OF THE INVENTION

The present invention relates to a dental composite carrier, an ampule for prepackaging composite material, and a package which makes possible contamination free storage of the composite and provides for easy handling of the composite.

1. Prior Art

Karter et al, in U.S. Pat. No. 3,735,492 teach a lever type dental amalgam carrier in which the amalgam tips are unitized rapidly interchangeable operating ends, which are adapted to be replaced when a tip becomes defective. While a particular amalgam tip is in use, amalgam is dispensed through the tip by pressing a lever 13 which causes plunger 12 to slide upward along a rod 11.

Hager & Werken catalog, 1984/1985, at page 10, illustrates an amalgam carrier which is used to carry an amalgam after it is prepared, said package comprising a cylindrical well used to hold amalgam, and a plunger which the amalgam carrier uses to force the amalgam out of the package. The amalgam package has threads and the amalgam carrier has a threaded end to which the amalgam package is threaded when used.

2. Background

This invention relates to a composite carrier used for holding and dispensing a polymeric material into a tooth cavity, a composite reservoir which is used with the carrier, and a convenient packaging system for said composite reservoirs. The present invention is particularly adapted for use with light activated composite materials.

Polymeric composites are increasingly gaining acceptance as a substitute for mercury/silver amalgams as a tooth filling material.

In the past, numerous organic compositions have been tried in various mixtures and proportions in order to find a satisfactory composition for use as dental composites or restoratives. These compositions have usually included some type of resin, which may either be preblended or mixed by the practitioner in the office. Dental composite and restorative materials must have good forming characteristics so that they can be shaped to fit a cavity area or molded into place in order to repair chipped or damaged teeth, yet such compositions are generally filled with inorganic materials in order to achieve satisfactory hardness and durability. Consequently, such materials, though moldable, are generally very stiff.

In the case where a preblended composite is provided, the composite is usually packaged in volumes sufficient for multiple uses and the dental practioner is required to either mix two ingredients, when a self cure composite is used, or to remove the composite from the package and use it very quickly, in the case where a light activated composite is used. An approach to this problem is the use of prefilled ampules of the kind represented by, for example, U.S. Pat. No. 4,391,590. The ampules described in the patent are especially useful for lower viscosity materials, but high viscosity materials of the kind used for posterior restorations are not expressed conveniently from such packaging. Since composite materials used as posterior restoratives are desirably very stiff to permit packing and condensing into cavities, special packaging is desirable which provides mechanical means for removing the composite from the package, for example, a bulk syringe, or the package may be provided with a wide opening, such as in a jar, so that the composite can be removed with a spatula. The composite material must then be delivered to the cavity preparation by an amalgam carrier or plastic placement instrument.

These methods of packaging have disadvantages in that when such a stiff material is extruded from bulk packages, it is hard to control the amount of material that is delivered and waste occurs. Also, if the bulk syringe tip becomes clogged, the whole package may have to be discarded.

Similarly, in a package having a large opening, as for example, a jar or tub from which composite is removed with a spatula, extreme care must be taken that the package contents are not contaminated while removing composite from the package. Repeated opening of a jar in a lighted room can also cause premature polymerization of the composite material. Also, when such a package is used, air can be introduced into the package material when a portion is being obtained which results in the introduction of air voids and undesirable porosity.

This method of packaging has the additional disadvantage that the dental technician, after removing the composite from the package, must somehow manipulate the composite onto a carrying device whereby the dentist can deliver the composite effectively to the tooth.

Accordingly, there is a need in the art for an apparatus that provides a convenient, easy, ready to use method of handling a high viscosity composite that is to be used as a dental restorative in incremental portions that are particularly suitable for direct use as a restorative that provides minimum handling of the composite by providing direct access and delivery, and that substantially eliminates the possibility of contamination and prepolymerization of the composite and thereby substantially reduces or eliminates unnecessary waste of material.

SUMMARY OF THE INVENTION

It is the object of the present invention to overcome the above described problems in the art.

The present invention provides a dental composite carrier comprising an elongated handle for carrying a composite to a tooth and depositing the composite in the tooth, and an elongated lever pivotally attached at one end of the handle, said lever having an end oriented over the handle and a notched and grooved end extending beyond the end of the handle. The notched and grooved end comprises a jaw which is adapted to pick up and hold a composite ampule. The dental composite carrier may have a condenser on the end of the handle distal from the lever for compressing and compacting the composite material into a tooth.

A composite ampule comprising a reservoir, said reservoir having a collar, and a plunger movable within the reservoir, the collar being adapted to be used as a holding means for the reservoir, is provided.

A package for a composite comprising a composite ampule comprising a composite reservoir and a plunger, wherein the reservoir is open at one end and a plunger is received in the other end; a tray having an upper surface and a lower surface and mounting stations in the upper surface, each mounting station being adapted to receive a composite ampule in the upper surface of the tray, and having a composite ampule received therein, and a layer of opaque material attached to the lower surface of the tray is also provided.

Also provided is a method of depositing a composite comprising the steps of containing a composite within a composite ampule comprising a reservoir having a collar on one end thereof, said reservoir having a hole therethrough, and a plunger extending from said hole; distributing a composite ampule on a tray whereby the compule is held upright in the tray with the plunger extending upward; picking up the ampule with a composite carrier having an elongated handle and an elongated lever attached to the handle, wherein the lever has a jaw at one end comprising a pair of J-bars adapted to hold the collar of an ampule, and a ram adapted to press the plunger; carrying the composite ampule from the tray to a tooth to be filled using the composite carrier; and pressing the composite reservoir against a tooth and pressing the lever with the forefinger, causing the handle and lever to pivot relative to each other and causing the ram to press the plunger, said plunger forcing the composite to exit from the open end of the reservoir and be deposited in the tooth.

The present invention provides a means of storing a composite in a closed environment and minimizes the chance of contaminating that environment by storing composite in individualized reservoirs and storing these reservoirs in individualized cells or mounting stations in a tray. Using a composite carrier to pick up an ampule from the tray and deliver the ampule containing the reservoir to a tooth minimizes manual handling of the composite, reduces labor and chances of contamination, prevents premature exposure to light, and minimizes the chances of porosity being introduced into the material. The spent ampule can be disposed of immediately, thereby also reducing contamination of the work place. Since the ampule is designed to hold about 20% to 100% of the correct amount of composite necessary to fill a tooth, there is a reduction in the amount of composite material wasted.

BRIEF DESCRIPTION OF THE DRAWINGS

FIG. 1 illustrates a top view of a composite package of the invention.

FIG. 2 illustrates a side view of the composite package of the invention.

FIG. 3 is a cutaway side view which illustrates the snap fit relationship of the top and the bottom of the tray and an ampule in a mounting station in the tray.

FIG. 4 is a top view of the lever of the composite carrier of the invention.

FIG. 5 is an end view showing the J-bars of the jaw of the lever holding an ampule.

FIG. 6 is an exploded side view of the dental composite carrier of the invention having a lever.

FIG. 7 illustrates a side view of a composite carrier holding an ampule of the invention.

FIG. 8 illustrates the ram of the composite carrier pressing down a piston of a composite ampule in the method of the invention.

DESCRIPTION OF THE PREFERRED EMBODIMENT

Referring now to FIGS. 4 and 6, the illustrated dental composite carrier of the invention 10 comprises an elongated handle 30, a lever 16 which pivots on said handle and ram 18 which is attached to handle 30 and elevated above handle 30 through neck 32. In the illustrated embodiment handle 30 contains a cavity 38 in each end for receiving an attachment, and ram 18 comprises a part of attachment 15 which is held in handle 30 when stem 36 of attachment 15 is snapped into cavity 38. In the illustrated embodiment lever 16 is attached to and pivots on attachment 15. Pin 13 on attachment 15 keeps lever 16 from sliding in relation to attachment 15, by fitting into pin hole 11 of lever 16. Point 19 on the attachment acts as a fulcrum point for lever 16 and is the point on which lever 16 pivots. Lever 16 is bow shaped upward so that when end 17 of lever 16 is pressed downward the jaw 12 of the lever moves upward toward ram 18. The bottom of the lever is slotted longitudinally so that the lever fits down on and partially surrounds attachment 15. Lever holder 34 holds lever 16 in place on attachment 15.

In the preferred embodiment, lever holder 34 will be an integral part of attachment 15. In an alternative embodiment, lever holder 34 may be separate from attachment 15 and will fit on attachment 15 by sliding over stem 36. Thus, lever 16 will fit on attachment 15 being held by pin 13 on attachment 15 being inserted into pin hole 11 of lever 16. Lever holder 34 will hold lever 16 onto attachment 15 with hook 31 of lever holder 34 snapping onto ridge 9 of lever 16. Arm 35 of lever holder 34 is substantially rigid but has sufficient flexibility to snap over ridge 9. In the illustrated embodiment, handle 30 may be provided with a condenser attachment (not shown) which has a stem which is received by a cavity similar to 38 on the opposite end of handle 30. The condenser attachment is adapted to compress and smooth filling material in a tooth.

With reference now to FIG. 5, jaw 12 of lever 16 comprises a pair of J-bars 40 which are formed when first notch 42 is cut or molded into lever 16 through its central axis on a plane substantially parallel to neck 32, and a second notch 44 is cut or molded into lever 16 on a plane substantially perpendicular to neck 32.

In the illustrated embodiment, each J-bar 40 is the shape of a squared J. Those skilled in the art will recognize that other modifications of the J-bar may be used in the jaw 12, such as, for example, a rounded J.

Similarly, in an alternative embodiment, jaw 12 may comprise two arms having ridges on the inside surfaces thereof, adapted to fit into a slot on the sides of an ampule 25.

With reference now to FIG. 4, J-bars 40 are particularly adapted to hold a collar 20 of a composite ampule 25. A composite ampule 25 comprises a composite reservoir 24 having a piston 22 therein which is adapted to move in said reservoir 24 in the direction of oriface 28 which causes a composite 26 which is stored in reservoir 24 to be forced out of oriface 28.

Collar 20 is adapted to be a holding means for holding an ampule 25 in jaw 12. Those skilled in the art will recognize that other holding means may be provided on ampule 25, such as a slot in the sides thereof which may be held by ridges in a jaw 12, that is adapted to pass on both sides of ampule 25.

Referring now to FIG. 3, in the illustrated embodiment reservoir 24 of ampule 25 has an enlarged upper interior portion 27 and a smaller lower interior portion 21. Piston 22 has a flange 23 which has a diameter substantially similar to the inside diameter of upper interior portion 27. The actuating stem 94 of the piston 22 is tapered so that its largest diameter is near flange 23. The plunger 96 of piston 22 is in the shape of a cylinder and is designed to substantially fill lower portion 21 of reservoir 24. Stop means 29 are provided in the top of upper interior portion 27 for stopping and preventing removal of piston 22 from reservoir 24. Similarly, shoulder 92 defining the area where upper interior portion 27 and lower interior portion 21 meet serves to act as a stop for flange 23 which limits the downward movement of piston 22.

In the preferred embodiment the stop means comprises ring 29 which completely circumscribes upper interior portion 27 of reservoir 24. Ring 29 is adapted to be distorted toward the interior of the reservoir 24 so that when an ampule 25 is assembled, the flange 23 of piston 22 displaces ring 29 to a degree sufficient to permit entry of flange 23 into upper interior portion 27 of reservoir 24. Ring 29 does not distort outwardly and therefore captures flange 23 within the reservoir 24.

With reference now to FIGS. 1–3, composite ampule 25 is preferably part of a package 50. Package 50 comprises a tray 51 which has an upper surface 54. Upper surface 54 is provided with a number of mounting stations 52 for holding ampule 25.

In the preferred embodiment, tray 51 will comprise a top 56 and a bottom 58 which will have a snap fitting relationship. In the illustrated embodiment bottom 58 has a hook snap 64 which is adapted to engage wedge 62 of top 56. Top 56 also has mounting station 52 which includes well 68 which is adapted to fit into or against receiving means 66 in bottom 58. It is preferred that ampule 25 be of sufficient length so that oriface 28 contacts bottom 58 to provide additional sealing of composite 26.

Top 56 further has an edge 74 which is of a dimension suitable for a sealing fit inside lip 72 of bottom 58. Bottom 58 is preferably made of an opaque material which prevents light from reaching and precuring the composite 26. The above described package arrangement substantially prevents light, dust, air and other contaminants from contacting composite 26. Also, since each ampule is situated in individual mounting stations which are also substantially sealed, introduction of contaminants into the package when portions of the composite are used is substantially prevented.

Ampules 25 may be provided in a number of sizes. Since it is preferable to fill a tooth with composite in several stages by curing small amounts of composite in the tooth and adding more composite as needed in incremental portions, to assure even curing of the composite mass, the ampules will be provided in sizes which provide for optimum cure of the composite.

Although a number of methods may be used for prepackaging composite material within an ampule, in the preferred embodiment this will be done by mass production. In the illustrated embodiment, the mounting stations 52 will comprise 4 rows and 5 columns, the rows being spaced with the center rows being closer than the outer rows so that the tray can be manipulated by using automated equipment which slides lifters between the inner and outer rows. The tray 51, in the upright position will first be loaded with twenty reservoirs 24, and twenty pistons 22 will be inserted therein. The tray 51 will then be inverted, and composite material will be loaded into the twenty ampules simultaneously. The bottom 58 of the tray is then attached, which prevents air and light from contaminating composite 26 at oriface 28 of ampule 25. Ring 29 prevents the pistons 22 from falling out of the ampules 25 when inverted, and ring 29, together with flange 23 also provides a seal which helps prevent air and light from entering reservoir 24 around piston 22.

With reference to FIGS. 7 and 8, in the method of the invention composite carrier 10, using J-bars 40 on jaw 12, is used to pick up ampule 25 by sliding J-bars 40 over collar 20 of ampule 25. To facilitate the picking up of ampule 25, jaw 12 of lever 16 is preferably angled above the axis of handle 30. Since a greater angle may reduce the ability of the practitioner to deposit the composite in a tooth, said angle will preferably be between 3 and 6° and most preferably will be about 4 ½°. Mounting stations 52 in tray 51 are spaced so that a single ampule 25 can be picked up easily without interference from adjacent ampules. Ampule 25 is removed from tray 51 and carried in jaw 12 to the place where composite 26 is to be deposited in the mouth. Oriface 28 of reservoir 24 is placed against the tooth where composite 26 is to be deposited, and lever 16 is pressed with the forefinger, causing handle 30 and lever 16 to pivot in relation to each other while lever 16 is held relatively stationary by the resistance of the tooth against reservoir 24. As handle 30 and lever 16 pivot about point 19, ram 18 contacts piston 22 of ampule 25. As pivoting continues, the movement causes ram 18 and jaw 12 to become close to each other, and since jaw 12 holds collar 20 of ampule 25, this causes ram 18 to force piston 22 into reservoir 24. As piston 22 enters reservoir 24, composite 26 is forced out of oriface 28 and into the tooth.

The dimensions of the ampule 25 and piston 22 are such that the extreme end 98 of plunger 96 extends beyond oriface 28 when the piston 22 has been pressed to the point where flange 23 is stopped by shoulder 92. By providing that plunger 96 extends beyond the end of reservoir 24 when composite 26 is delivered, the surface of ampule contacting composite 26 is minimized, and this ensures that composite 26 will adhere to the tooth cavity in preference to remaining in the end of the ampule.

The composite carrier 10 can then be removed from the mouth and the empty ampule 25 discarded. The composite carrier can then be turned and the condenser attachment can be used to compress, compact and smooth composite 26 in the tooth.

As an alternative to having a condenser on one end and a jaw and lever on the other end, some practitioners may prefer to use the composite carrier with a jaw and lever on both ends which he may use to carry two ampules to the tooth at once. The condenser attachment may then be removed and replaced with a lever attachment. The attachments are preferably made with a positive snap lock fit so that the practitioner can easily determine when the attachment is in position on the handle. The mouth of cavity 38 in handle 30 will be relatively wide to make it easy for stem 36 to be inserted into cavity 38, and the channel in cavity 38 will narrow to a recess seat to provide said snap lock fit.

The composite carrier of the invention, and the method in which it is used makes it possible to fill a tooth using a composite with minimum handling of the composite. The invention provides a means and a method for insuring that the composite used has minimal contamination from outside sources and provides means to prevent undesirable precure of the composite.

The composite carrier of the invention can be made relatively inexpensively. Preferably, the handle and the stem portions of the attachments and the lever may be made of plastic.

The attachments can be removed from the handle for sterilization or the whole instrument may be sterilized using cold sterilization. Also, in the case where the instrument is made of microwave compatible plastic, microwave sterilization can be used. Ethylene oxide sterilization, irradiation with gamma radiation or other conventional means of sterilization may also be used.

In addition to the embodiments described above, one skilled in the art will recognize that the ampule and jaw of the lever may be adapted for other means of picking up the ampule. For example, the ampule may be made with a rough outer surface which is adapted to mesh or interlock with a rough surface on the jaw. Or the jaw may be made with a snap ring which fits over the ampule and allows for a vertical approach to the ampule with the composite carrier. Other means for picking up an ampule with the lever of the composite carrier will be apparent to those skilled in the art.

Although as illustrated, the composite carrier of the invention has a handle adapted to receive lever and condenser attachments, it will be recognized by those skilled in the art that the present invention may be practiced wherein the lever, and optionally the condenser, form a single construction with the handle.

Although described for use primarily with a posterior composite, those skilled in the art will recognize that the present invention may also be used with other types of composites.

While a specific embodiment of the present invention has been illustrated and described, those skilled in the art will recognize that the invention may be otherwise variously practiced without departing from the inventive concept illustrated by the following claims.

What is claimed is:

1. A package for a composite comprising: a plurality of composite ampules, each said ampule comprising a composite reservoir and a piston, said reservoir being open at one end and having a piston received in a distal end; a tray for storing said ampules having a top part having an upper surface and a lower surface said top part having mounting stations therein, each said mounting station being adapted to receive a composite ampule in said upper surface of said tray and having composite ampules received therein for storage, said mounting stations being adapted to permit easy removal of said ampules therefrom when said ampules are used.

2. The package for a composite according to claim 1, wherein said tray comprises a top part and a bottom part, said top and bottom parts being adapted to snap together in a sealing manner.

3. The package for a composite according to claim 1 in which said mounting station is adapted to hold said ampule in said tray in a substantially closed environment.

4. The package for a composite according to claim 3 in which said mounting station in said top part of said package is adapted for contact with said bottom part of said package.

5. A method for depositing a composite comprising the steps of:
    (a) prepackaging composite within a composite ampule comprising a reservoir having a single hole therethrough, a collar on said reservoir, and a piston extending from said hole in one end of said reservoir, said reservoir having an open end;
    (b) distributing a plurality of said composite ampules in a mounting stations in a tray whereby said ampule is held upright in said tray for storage with said piston extending upward;
    (c) picking up an ampule from said tray using a composite carrier having an elongated handle having an elongated lever pivotally attached thereto, said lever having one end comprising a jaw having a pair of J-bars adapted to hold said collar; and a ram adapted to press said plunger;
    (d) carrying said composite ampule from said tray to a tooth to be filled with said composite using said composite carrier; pressing said composite reservoir against a tooth and moving said lever, thereby causing said handle and lever to pivot relative to each other and said ram to press said piston, said piston forcing said composite to exit from said open end of said reservoir; and depositing said composite to said tooth.

* * * * *